(12) United States Patent
Roy

(10) Patent No.: US 6,705,585 B1
(45) Date of Patent: Mar. 16, 2004

(54) MULTI-PURPOSE VALVE

(76) Inventor: Sumit Roy, Industrigt. 7A, Oslo (NO), N-0357

( * ) Notice: Subject to any disclaimer, the term of this patent is extended or adjusted under 35 U.S.C. 154(b) by 0 days.

(21) Appl. No.: 09/869,315

(22) PCT Filed: Feb. 16, 2000

(86) PCT No.: PCT/NO00/00057

§ 371 (c)(1),
(2), (4) Date: Oct. 24, 2001

(87) PCT Pub. No.: WO00/48533

PCT Pub. Date: Aug. 24, 2000

(30) Foreign Application Priority Data

Feb. 17, 1999 (NO) .......................... 1999 0736

(51) Int. Cl.⁷ .............................................. F16K 31/64
(52) U.S. Cl. ............................ 251/11; 251/902; 604/34
(58) Field of Search ................... 251/11, 902; 148/402; 604/34

(56) References Cited

U.S. PATENT DOCUMENTS

| | | | |
|---|---|---|---|
| 4,544,599 A | 10/1985 | Buttazzoni | .................. 428/262 |
| 4,899,543 A | 2/1990 | Romanelli et al. | ............. 60/527 |
| 5,037,427 A * | 8/1991 | Harada et al. | ............... 606/108 |
| 5,242,451 A * | 9/1993 | Harada et al. | ............. 623/1.18 |
| 5,500,014 A | 3/1996 | Quijano et al. | ................. 623/2 |
| 5,562,641 A * | 10/1996 | Flomenblit et al. | ......... 604/531 |
| 5,653,759 A | 8/1997 | Hogan et al. | .................. 623/11 |

FOREIGN PATENT DOCUMENTS

| | | |
|---|---|---|
| DE | 4204138 C2 | 8/1993 |
| DE | 19531659 C2 | 3/1997 |
| EP | 0145166 B2 | 6/1985 |
| FR | 1461567 | 10/1965 |
| FR | 1464202 | 12/1965 |
| FR | 7733485 | 6/1979 |

* cited by examiner

Primary Examiner—John Bastianelli
(74) Attorney, Agent, or Firm—Jacobson Holman PLLC

(57) ABSTRACT

A multi-purpose valve includes, a band of a thermodynamic metal alloy with shape memory, with a memorised shape and a transition temperature which lies in the range for the normal body temperature of a mammal. The strip has a linear shape below the transition temperature and assumes the memorised shape above the transition temperature. The memorised shape is preferably a conical spiral with a closed tip, with the result that above the transition temperature range the valve will become a conical spiral.

4 Claims, 3 Drawing Sheets

MULTI-PURPOSE VALVE

BACKGROUND OF THE INVENTION the present invention relates to a multi-purpose valve for use as a therapeutic device, comprising a band having when in situ the shape of a conical spiral formed by multiple, successive, helical turns, in such a way that at a first pressure difference across the valve, the helical turns of the band abut one another and seal the cone, whereas at a second pressure difference across the valve, which is larger in the direction towards the tip of the conical spiral than the first pressure difference, the valve is extended axially such that said turns separate from another so as to allow flow therebetween.

The multi-purpose valve according to the invention is designed for the treatment of chronic, venous insufficiency secondary to primary valvular incompetence or post-thrombotic syndrome. Furthermore, the device can act as an inexpensive alternative to artificial heart valves which are in use and as a sphincter at cxaravascular locations such as the urethra and the pylorus.

Venous valves are crucial for normal blood flow in the lower extremities. Damage to these structures is a common result of thrombosis, leading to the development of post-thrombotic syndrome, a common, chronic and often disabling disease.

Surgical reconstruction of venous valves is a technically demanding procedure and therefore has achieved only limited acceptance in clinical practice. Thus there is a clear need for an artificial valve which can be implanted in the veins.

In addition to this, there is a need for artificial heart valves which can be implanted through the skin, and sphincteric devices which can be placed in the urethra and the pylorus.

Some bioprosthetic valves have been developed for use as venous valves (e.g. U.S. Pat. No. 5,500,014) but none of them has been found suitable for clinical application. These devices consist substantially of a rigid metal ring covered by a biocompatible polymer. Heart valve flaps from pigs or flaps designed from bovine pericardium which are attached by means of glutaraldehyde are secured by sutures to the metal ring. The main advantage of these devices is that they are based on a concept which has been tried and tested in the heart. However, this advantage must be weighed against the risk which is involved in using animal tissue. Bioprosthetic valves, moreover, have a limited life due to the degenerative changes which inevitably follow implantation. The bioprosthetic valves have only been tested as venous valves in vitro or in the largest central veins in non-primate mammals. Thus their real thrombogenic potential is still Sown.

Another known valve is a metallic flap disc valve (developed at Millard Fillimore Hospital by Taheri et. al.). This valve has been shown to be unsatisfactory.

DE-A-4204138 (Zimmermann et. al.) describes an artificial valve comprising two or more wires in spiral configuration which are attached to a rigid ring. While this invention is free of some of the drawbacks listed bove, its function is dependant on arterial haemodynamics, making it unsuitable as a substitute for venous valves. In addition, the ring precludes the possibility of implanting the valve by a non-surgical percutaneous approach.

SUMMARY OF THE INVENTION

These and other problems related to the known devices are solved by means of the multi-purpose valve according to the invention. This valve is characterized in that the valve is constituted by one single band of a thermodynamic metal alloy with shape memory, with said conical shape as a memorised shape, and with transition temperature in the range for the normal body temperature of a mammal, (35–41 degrees Celsius) with the result that the band has a linear shape below the transition temperature and assumes the memorised, conical shape above the transition temperature, making the valve percutaneously implantable.

In a further preferred embodiment of the invention, the band is provided on one surface with flexible, highly magnetic strips and on the opposite side with ferromagnetic strips. This feature permits prostheses to be manufactured with different opening pressures simply by altering the pole strength of the magnetic strips.

The valve according to the invention is designed by winding a thin, narrow band of a thermodynamic metal alloy with shape memory (e.g. Nitinol) round a mould with a suitable shape and heat treating it. The alloy is characterized by long-term stability under cyclic loading, and its transition temperature lies below the normal body temperature, All metallic surfaces are preferably covered with a biocompatible, bistable, non-thrombogenic polymer layer. Below the transition temperature range, the thermodynamic metal is in a martensitic state and the device has a linear shape. Above the martensitic transition temperature range the metal band is transformed to austenitic state, thereby recovering the memorised shape which it received during heat treatment.

Another important feature of the invention is that it permits transcatheter implantation through the skin, on account of the band's linear shape before it reaches normal body temperature. The band with its linear shape can easily be inserted in the body and subsequently, when the transition temperature is reached, it will assume a valve shape.

The valve according to the invention can be manufactured from freely available materials, and it does not include animal tissue of any type. This eliminates the risk of transferring zoonotic infections and of causing undesirable immune reactions.

In a preferred embodiment the whole device is covered with a biocompatible, non-thrombogenic, biostable polymer (e.g. low-molecular-weight dimer of parachloroxylene (parylene), thus eliminating the risk of chemical interaction between the substrate and the blood. Human cells proliferate rapidly and easily on the parylene-coated surface to produce thin adhesion layers of morphologically normal tissue. Thus rapid endothelium cover of the prosthesis according to the invention can be predicted, thereby minimising the risk of de novo thrombosis.

BRIEF DESCRIPTION OF THE DRAWINGS

The invention will now be described by means of an illustrating and non-limiting embodiment, which is illustrated in the following drawings, in which.

DETAILED DESCRIPTION OF THE INVENTION

Figure 1:
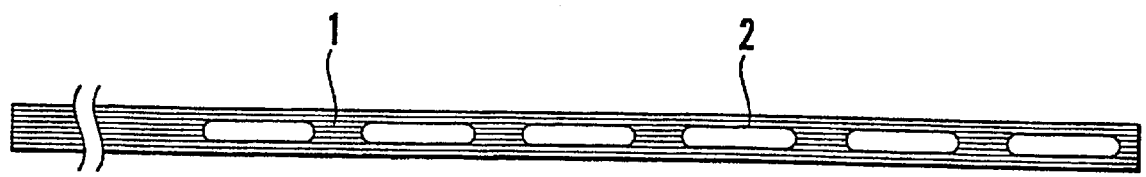
FIGS. 1 and 2 illustrate the valve according to the invention in a state below transition temperature.

FIG. 1 illustrates the valve according to the invention in a state below the transition temperature range of the thermodynamic material. This figure illustrates what will be the valve's outer surface when the temperature has increased above the transition temperature range. As already mentioned, in "the low temperature state" the valve consists of a thin, narrow band 1 of a thermodynamic metal alloy with shape memory (e.g. an echiatomic nickel-titanium, intermetallic alloy such as nitinol), characterized by long-term stability under cyclic loading. The valve's outer surface is provided with highly magnetic strips 2 with a high degree of remanence.

Figure 2:
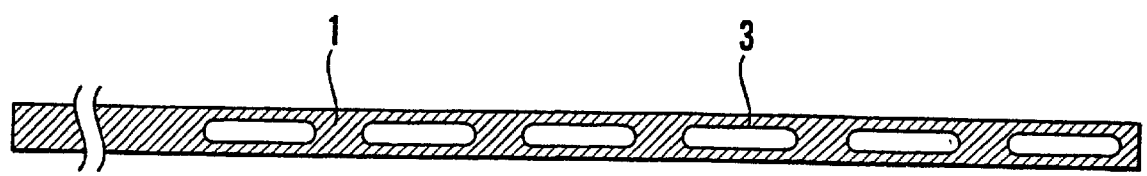

FIG. 2 illustrates what will form the inner surface of the valve according to the invention, in a state below the transition temperature. On this side the band 1 is provided with ferromagnetic strips 3.

The magnetic strips on both sides of the band have a direct influence on the valve's pressure gradient for opening and closing by providing magnetic attraction forces between helical coils located in the immediate vicinity of one another.

Figure 3:
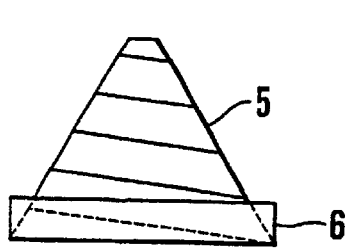
FIG. 3 illustrates the valve according to the invention in a state above the transition temperature and closed.

FIG. 3 illustrates the valve above the transition temperature range for the thermodynamic metal and closed. The valve's body 5 consists of a plurality of successive coils which partly overlap one another, thereby forming a hollow cone. The last coil or "connecting part" 6 is a single coil which is located in a plane at right angles to the body's 5 longitudinal axis and continuous with the part 5.

Figure 4:
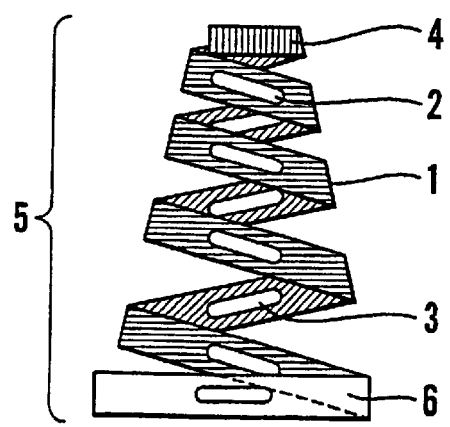
FIG. 4 illustrates the valve according to the invention in a state above transition temperature and open.

FIG. 4 illustrates the valve above the transition temperature range for the thermodynamic metal and open. The "nose" or the top 4 of the valve comprises a plurality of successive coils which overlap one another completely, forming a flat spiral which closes the cone, and which is continuous with the valve's body 5.

Figure 5A:
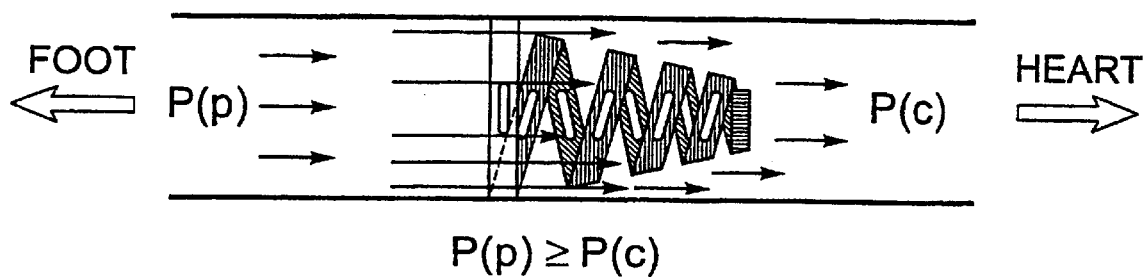
FIGS. 5a and 5b illustrate use of the valve according to the invention in leg veins.

The main function of the valve according to the invention, both in the vein (FIGS. 5a, 5b) and heart (FIG. 6) embodiments is to ensure one-way flow, the temporal pattern of which varies according to the anatomical location. In the leg veins the preferred direction for blood flow is towards the heart, and the temporal pattern is substantially continuous with occasional interruptions. It is therefore important for an artificial venous valve to remain open as long as there is a pressure gradient in the direction of the heart, and to close quickly when this gradient is reversed.

Figure 5B:
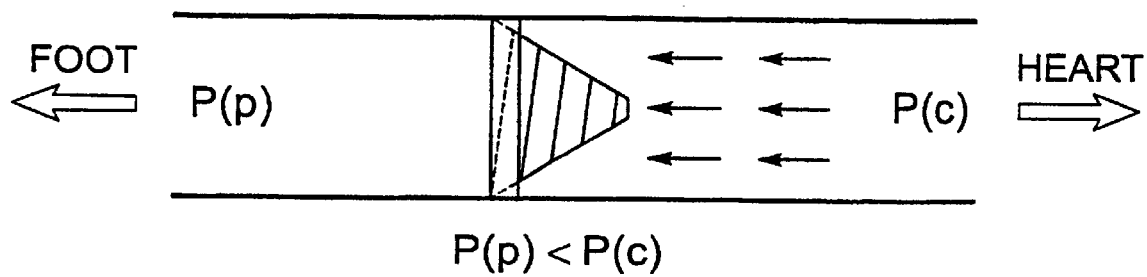

In the venous embodiment (FIGS. 5a, 5b), the adjacent strips in the multipurpose valve according to the invention will not overlap one another (i.e. they will remain open) in the absence of external axial forces. Axial forces acting along the vector between the connecting part and the "nose" will further distract adjacent turns of the spiral. Since the valve will be placed with its "nose" facing the heart, it will remain open in the presence of a pressure gradient in the direction of the heart (vein→heart), (FIG. 5a, P(p)>P(c), where P(p)=intraluminal pressure peripheral to the valve, P(c)=intraluminal pressure central to the valve). When the direction of the pressure gradient is reversed (heart→vein), as is the case when a person rises, axial forces oriented along the "nose to connecting part" vector will act on the valve, laying each coil overlappingly on its immediately underlying neighbour, thereby causing the valve to be closed (FIG. 5b). This process is facilitated by the attractive force exerted by the magnetic strips on the adjacent ferromagnetic counterparts.

Figure 6:
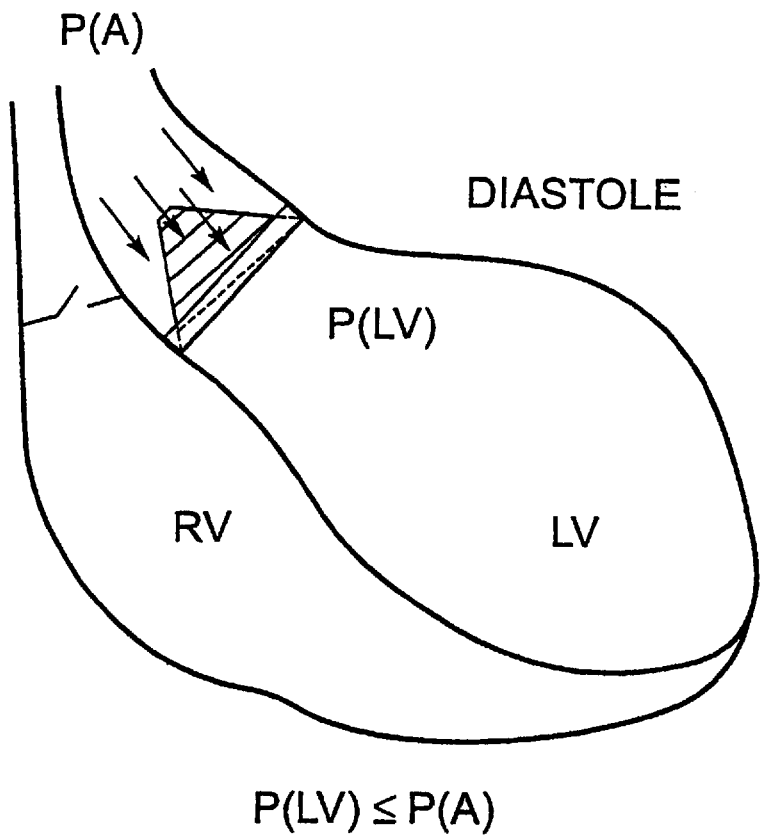
FIG. 6 illustrates use of a valve according to the invention as an aortic valve.
Figure 6:
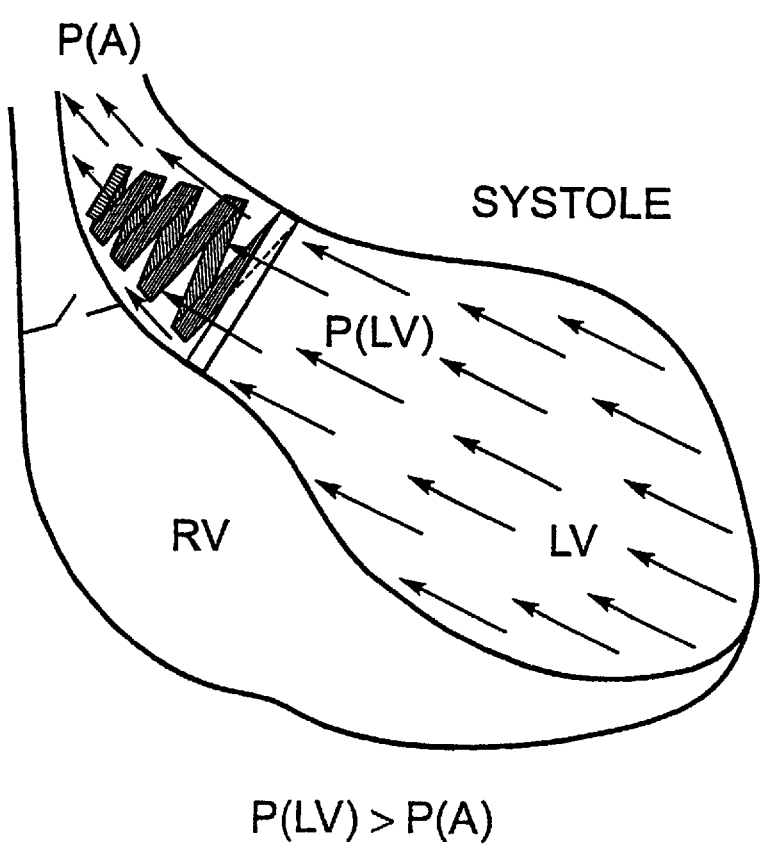

In contrast to this, in heart (FIG. 6) and extravascular embodiments, the valve will remain closed in the absence of external axial forces, since in these anatomical locations the normal flow temporal pattern are invariably intermittent. However, in the same way as for the veins, the valve's physical state (open/closed) at a given point of time will be determined by the internal pressure gradients. FIG. 6 illustrates the multi-purpose valve according to the invention in the aorta location. In this case the pressure gradient is the difference between left ventricular pressure (P(LV)) and aortic pressure (P(A)).

In a preferred embodiment of the invention (not shown) which is suitable for surgical use, the system for affixing the valve comprises a series of holes which are drilled in the connecting part through which sutures can be passed.

In a second preferred embodiment of the invention (not shown), which is suitable for transcatheter use, the system for affixing the valve comprises a series of barbs attached to the connecting part's outer surface or an expandable vascular stent.

The multi-purpose valve according to the invention is entirely free of joints. The possibility of structural defects during long-term use will thus be much smaller than, e.g., for the bioprosthetic valve. In contrast to the latter, the design of the valve according to the invention is suitable for automated manufacture, thus simplifying the manufacturing process.

The possibility of transcatheter implantation through the skin is one of the greatest advantages of the valve according to the invention compared to all the artificial heart valves in use. The same applies in comparison to applications as a urinary sphincter.

The valve according to the invention therefore opens the possibility of valve replacement even for patients who will not be able to withstand major surgery.

In contrast to the artificial urethra sphincters which are in use, the valve according to the invention resembles the ordinary urethra sphincter in the manner that its function will be modulated by the bladder pressure.

What is claimed is:

1. A multi-purpose valve (5) for use as a therapeutic device, comprising a band (1) having when in situ the shape of a conical spiral formed by multiple, successive, helical turns, in such a way that at a first pressure difference across the valve, the helical turns of the band abut one another and seal the cone, whereas at a second pressure difference across the valve, which is larger in the direction towards the tip of the conical spiral than the first pressure difference, the valve is extended axially such that said turns separate from another so as to allow flow therebetween, characterised in that he valve is constituted by one single band (1) of a thermodynamic metal alloy with shape memory, with said conical shape as a memorised shape, and with transition temperature in the range for the normal body temperature of a mammal, with the result that the band has a linear shape below the transition temperature and assumes the memorised, conical shape above the transition temperature, making the valve percutaneously implantable.

2. A multi-purpose valve according to claim 1, characterized in that the thermodynamic metal alloy with shape memory is Nitinol.

3. A multi-purpose valve according to claim 1, characterized in that the band (1) is provided on one surface with flexible magnetic strips (2) of strong magnetic force and on the other surface with ferromagnetic strips (3), said strips being arranged so as to cooperate for effecting or enhancing the attraction or separation of the spiral turns of the band.

4. A multi-purpose valve according to claim 1, characterized in that the band (1) is covered with a non-thrombogenic, biostable polymer, e.g. parylene.

\* \* \* \* \*